United States Patent [19]

Kelly et al.

[11] Patent Number: 5,312,904
[45] Date of Patent: May 17, 1994

[54] CATIONIC COMPLEXES OF TECHNETIUM-99M

[75] Inventors: James D. Kelly, Amersham; Kwok W. Chiu, Gloucester, both of England; David V. Griffiths, Keele; Jonathan R. Dilworth, Colchester, both of United Kingdom

[73] Assignee: Amersham International plc, Buckhamshire, United Kingdom

[21] Appl. No.: 879,098

[22] Filed: May 4, 1992

Related U.S. Application Data

[63] Continuation of Ser. No. 472,293, Jan. 30, 1990, abandoned.

[30] Foreign Application Priority Data

Feb. 3, 1989 [GB] United Kingdom ............... 8902362

[51] Int. Cl.$^5$ ............... A61K 49/02; C07F 13/00
[52] U.S. Cl. .................. 534/14; 424/1.65; 424/1.77
[58] Field of Search ............ 534/10, 14; 424/1.1, 424/9

[56] References Cited

U.S. PATENT DOCUMENTS

| | | | |
|---|---|---|---|
| 4,430,319 | 2/1984 | Blau et al. | 424/1.1 |
| 4,451,450 | 5/1984 | Subramanyam | 424/1.1 |
| 4,455,291 | 6/1984 | Tweedle | 424/1.1 |
| 4,481,184 | 11/1984 | Kronauge et al. | 424/1.1 |
| 4,489,053 | 12/1984 | Azuma et al. | 424/1.1 |
| 4,489,054 | 12/1984 | Deutsch et al. | 424/1.1 |
| 4,497,790 | 2/1985 | Rodriguez | 424/1.1 |
| 4,526,776 | 7/1985 | Subramanyam et al. | 424/1.1 |
| 4,795,626 | 1/1989 | Deutsch et al. | 424/1.1 |
| 4,916,214 | 4/1990 | Chiu et al. | 424/1.1 X |
| 5,112,595 | 5/1992 | Woulfe et al. | 424/1.1 |

FOREIGN PATENT DOCUMENTS

0123240 10/1984 European Pat. Off. .
0201005 11/1986 European Pat. Off. .

*Primary Examiner*—Robert L. Stoll
*Assistant Examiner*—John M. Covert
*Attorney, Agent, or Firm*—Wenderoth, Lind & Ponack

[57] ABSTRACT

Tridentate mono-anionic ligands have the structure

X-A-Y-Q-Z where each of X and Y is independently P, As or N,
Z is phenol, thiophenol or thiol, and
A and Q are hydrocarbon linking groups.

The ligands from cationic complexes with Technetium-99m, e.g. $[Tc^{III}K_2]^+$ where K is the ligand, having useful imaging properties.

7 Claims, No Drawings

CATIONIC COMPLEXES OF TECHNETIUM-99M

This application is a continuation of now abandoned application, Ser. No. 07/472,293, filed Jan. 30, 1990.

This invention relates to cationic complexes of technetium-99m (Tc-99 m) useful as body imaging agents, and to ligands for the formation of such complexes.

Radiopharmaceuticals may be used as diagnostic or therapeutic agents by virtue of the physical properties of their constituent radionuclides. Thus, their utility is not based on any pharmacologic action. Most clinically used drugs in this class are diagnostic agents incorporating a gamma-emitting nuclide which, because of physical or metabolic properties of its co-ordinated ligand, localizes in a specific organ after intravenous injection. The resultant images can reflect organ structure or function. These images are obtained by means of a gamma camera that detects the distribution of ionising radiation emitted by the radioactive species. The principal isotope currently used in clinical diagnostic nuclear medicine is the metastable technetium-99m (t½ 6 hours).

It is well established that neutral bidentate ligands of the general type $R_2Q(CH_2)_nQR_2$ (where Q may be phosphorus or arsenic, n is 2 or 3 and R is alkyl or aryl) form stable well characterised cationic complexes with Tc-99 and Tc-99m.

European patent application 201005 describes tridentate ligands in which the co-ordinating atoms are "hard" electronegative atoms such as N or O. Tc(V) complexes with one such tridentate ligand are described.

The present invention is concerned with tridentate mono-anionic ligands. These should be capable of giving rise to the cationic complex $[Tc(III)K_2]^+$, where K is the ligand, which should have valuable body imaging, and in particular heart imaging, properties.

The invention provides a tridentate mono-anionic ligand having the structure

R₂X-A-YR-Q-Z where
- X is a neutral donor which is P, As or N
- Y is a neutral donor which is P, As or N
- Z is a mono-anionic function which is phenolic OH, thiophenol or thiol,
- each of A and Q is a C1–C4 hydrocarbon bridge, two adjacent C atoms of which may form part of a benzene ring and which may carry at least one C1–C4 alkyl, alkoxy alkyl, alkoxy or tetrahydropyran substituent,
- R may be the same or different at different places in the molecule, and in each case is selected from C1 to C4 alkyl, alkoxy, alkoxyalkyl and alkoxyalkoxy alkyl.

Preferably, at least one of X and Y is P or As; for example, X may be P and Y may be N. Preferably A is —C₂H₄—. Preferably Q is a C2 or C3 bridge which may be substituted. The following are examples of ligands according to the invention, of which the last forms the subject of Example 1 below.

Ex. 1.

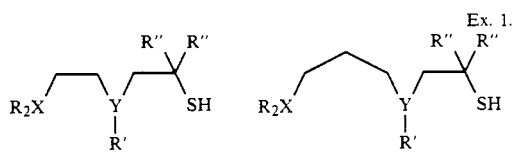

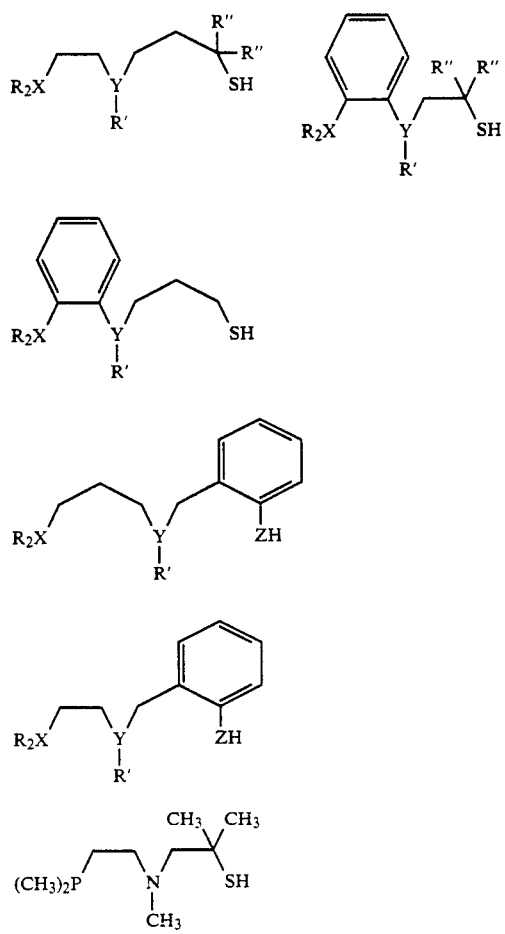

Where
- X is P or N,
- Y is independently P or N,
- Z is O or S,
- R, R' and R" may be the same or different at different places in the molecule, and each is H or hydrocarbon which may contain one or more ether linkages, such as $C_nH_{2n+1}$ (n=1, 2, 3), CH₂OMe, OMe, CH₂OC₂H₄OMe, C₂H₄OMe, CH₂OC₂H₅, branched alkyl. Two groups R" may together form a tetrahydropyran ring. Preferably, at least one of R, R' or R" contains at least one ether linkage.

The synthesis of the tridentate thiol ligands can be effected by reacting the corresponding secondary amine or phosphine with ethylene sulphide in toluene solution at 100° C. for approximately two hours:

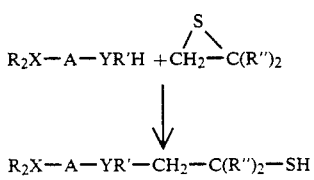

R₂X—A—YR'—CH₂—C(R")₂—SH

Where
R, R', R" and A are as defined above and
X is P and Y is P, or
X is N and Y is N X is N and Y is P, or possibly
X is P and Y is N.

For tridentate thiol ligands with propylene bridge A, a different synthetic route is appropriate

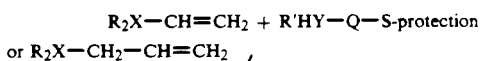

where
R, R' and A are as defined above,
Q is a propylene bridge, and
X is P and Y is P, or
X is N and Y is N, or
X is N and Y is P.

Where X is P and Y is N, the synthesis of the phosphine ligands can be carried out by reduction of the corresponding phosphine sulphides. These phosphine sulphides are accessible by the nucleophilic addition of suitably protected aminothiols across the vinyl groups in dialkylvinylphosphine sulphide as shown below. Addition of less basic aromatic amines across the vinyl group in the dialkylvinylphosphine sulphide can only be achieved after activation of the amine with strong base.

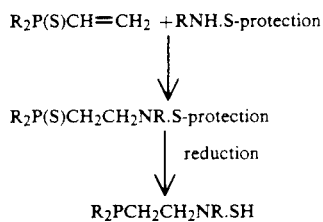

As protected amino thiols, there can be used amino disulphides, which can be prepared by known routes. For example, the preparation of 1-methylamino-2-methyl-yl-propane-2-thiol disulphide is described by Corbin (J. Org. Chem., 1976, 41, 489).

Tc-99 complexes of the ligands may be made by methods well known in the art. For example, a mixture of the ligand with a solution of pertechnetate (TcO$_4^-$) may be held for a short time in the presence of a reducing agent. Suitable reducing agents include tin metal and stannous salts. The mixture may be heated if necessary, but in many cases it is sufficient to allow the mixture to stand at ambient temperature for a short time, e.g. 5 to 60 minutes. Alternatively, the complex may be made by a process of ligand exchange, as well known in the field.

In another aspect, the invention also includes complexes of the ligand defined above with technetium-99 m. It is expected that the complex may have the formula [$^{99m}$Tc$^{III}$K$_2$]$^+$, where K is the ligand. Advantages of this aspect of the invention include:

a) the ease of labelling of the ligand to provide a 1-step room temperature synthesis of a cationic Tc-99 m complex.

b) Once formed, the complex is generally stable in aqueous and/or aqueous/ethanolic media in a form which is suitable for administration.

c) The complex may have useful body imaging, in particular heart imaging, properties.

In the experimental section, Example 1 relates to the preparation of a ligand according to the invention; Example 2 concerns the preparation and properties, including biodistribution in rats, of a Tc-99 m complex of that ligand; Examples 3, 4 and 5 relate to the preparation of three more ligands; and Example 6 concerns the preparation and biodistribution properties of a Tc-99 m complex of the ligand of Example 3.

EXAMPLE 1

Preparation of 1-(N-2'-Dimethylphosphinoethyl-N-methylamino)-2-methylpropane-2-thiol.

(CH$_3$)$_2$P(CH$_2$)$_2$ N(CH$_3$)CH$_2$C(CH$_3$)$_2$SH (whose structure is illustrated above).

i.

Bis-[2-(N-2'-dimethylphosphinothionylethyl-N-methylamino)-1,1-dimethylethyl] disulphide 1-Methylamino-2-methylpropane-2-thiol disulphide (3.4 g) in absolute ethanol (100 cm$^3$) was heated under reflux with dimethylvinylphosphine sulphide (3.6 g) for a period of about 2 weeks. The ethanol was then removed under reduced pressure and the residue chromatographed on a florisil column using ethyl acetate/petroleum ether mixtures as eluant. Although the disphosphorus disulphide isolated in this way was contaminated with the starting disulphide this latter material was removed by crystallisation from diethyl ether. The pure diphosphorus disulphide was isolated as a white solid, m.p. 74°-75° C. (4.1 g, 61%). Found: C,45.56; H, 9.10; N, 5.84. C$_{18}$H$_{42}$N$_2$P$_2$S$_4$ requires C, 45.35; H, 8.88; N, 5.88%.

$^{31}$P (CDCl$_3$)/$_{ppm}$35.9

$^{13}$C (CDCl$_3$)/$_{ppm}$21.2(d, J=54), 26.5, 32.3(d, J=52), 44.4, 50.9, 53.6, 67.8.

ii.

1-(N-2'-Dimethylphosphinoethyl-N-methylamino)-2-methylpropane-2-thiol

To a suspension of the diphosphorus disulphide (1 g) in dry dioxan (100 cm$^3$) was added lithium aluminium hydride (0.5 g). The resulting mixture was heated cautiously until an exothermic reaction occurred whereupon the heating was removed. When this exothermic reaction had subsided the reaction mixture was heated under reflux and the progress of the reaction monitored by $^{31}$P n.m.r. spectroscopy. When the reduction was complete the reaction was allowed to cool and wet dioxan was cautiously added (2.5 cm$^3$; 75% dioxan, 25% water). Aqueous sodium hydroxide (1 cm$^3$, 2M) and then water (1.5 cm$^3$) were added and the resulting mixture filtered under vacuum. The filtrate was evaporated under reduced pressure (60° C. at 100 mmHg) to give the phosphine ligand (0.42 g, 48%). Although this material was shown by n.m.r. spectroscopy to contain some dioxan it could be used without further purification.

$^{31}$P (CDCl$_3$)/$_{ppm}$-54.3

$^{13}$C (CDCl$_3$)/$_{ppm}$14.0(d, J=12), 30.1(d, J=10), 30.3, 44.3, 46.2, 56.9(d, J=19), 71.4.

EXAMPLE 2

Tc-99 m Complex of the Ligand of Example 1

Materials

| | |
|---|---|
| Ethanol | 2 ml |
| SnF$_2$ | 8 μg in 1 ml of water |

| | |
|---|---|
| Ligand | 20 μl |
| $^{99m}TcO_4^-$ | Generator Eluate 1 ml at 2.29 GBq/ml |

-continued

Methods

The components were mixed in a sealed $N_2$ purged vial and left standing at room temperature for 15 minutes. The resulting solution was then submitted to chromatographic analysis and animal biodistribution studies.

Chromatographic Data

The resulting preparation contains no free $TcO_4^-$ or technetium colloid, and indicates that the desired species is present in solution in approximately 90% yield. ITLC chromatography indicates only one major component present.

| | |
|---|---|
| Saline | rf = 0.07 |
| Methylethylketone | rf = 0.07, 0.61 |
| Acetonitrile:water 50:50 | rf = 0.96 |

HPLC Data

The complex elutes as a sharp peak at approximately 20.5 minutes with a small peak at 17 minutes (5–10%).

Gel Electrophoresis Data

The complex moves as a single band towards cathode rf = −0.67 (− indicates movement towards cathode).

Biodistribution Results

See Table.

Experimental

The experimental techniques used to characterise and evaluate this new radiopharmaceutical compound are outlined below.

Chromatography

Samples were supplied by needle approximately 2.5 cm from the bottom of two Gelman ITLC/SG strips and one Whatman No. 1 strip (2.5 cm × 20 cm) and then immediately placed in prepared ascending chromatography development tanks containing fresh solvent (1 cm$^3$)=a) saline, b) methylethylketone, and c) 50:50 acetonitrile:water respectively. After 15 cm elution and strips were removed, solvent fronts marked, dried and the distribution of activity determined using suitable equipment.

Electrophoresis

An 0.1 g Agarose/10 cm$^3$ 50 mM phosphate buffer pH 7.4 was run at an applied potential of 300 V for approximately 35 minutes, using bromophenol blue indicator (this indicator moves towards anode). The resulting distribution of activity was determined using suitable equipment.

HPLC

A solvent gradient HPLC system was used in conjunction with:

A) 0.1M sodium acetate + 0.001% cresol pH 5.5
B) Acetone

Samples are applied initially at 100% A and maintained at 100% A for 5 minutes, the gradient is then changed to 100% B in 15 minutes and maintained at 100% B for 10 minutes. The gradient is changed again to 100% A in 5 minutes and maintained for 5 minutes ready for next run. Flow rate is maintained steadily at 1 ml per minute. Hamilton PRP-1 Column (packed with poly(styrenedivinyl benzene) copolymers, 15 cm × 4.0 mm) at room temperature was used. Tc-99 m compound was detected by gamma counter.

Animal Biodistribution—In Vivo Studies

In vivo biodistribution: 0.1 ml was injected i.v. into a lateral tail vein of 6 anaesthetised rats.

At 2 minutes and 60 minutes post injection, three rats were sacrificed by decapitation, bled from the neck and dissected. The following organs were removed at dissection: kidney, bladder (+urine), lung, liver, spleen, stomach, small intestine, large intestine, brain (weighed), thyroid and samples of blood (weighed) and muscle (weighed), the residual carcass and the tail (injection site). Subsequently samples were counted in an automatic twin crystal gamma counter.

Percentage biodistribution of injected material was calculated (after correction for background) for all organs using the formula:

$$\% \text{ injected dose} = \frac{\text{counts/organ}}{\text{total count in animal} - \text{count in tail}} \times 100$$

Since only samples of muscle and blood were taken, the percentage in these tissues was calculated assuming blood and muscle to represent 5.8 and 43% of total animal weight respectively using the formula: % injected dose in $$\text{tissue} = \frac{\text{counts/gram tissue} \times CF \times \text{Bodyweight} \times 100}{\text{total counts in animal} - \text{total counts in tail}}$$

where CF = 0.058 for blood
         0.43 for muscle

| Animal Biodistribution Data in Rat | | | | |
|---|---|---|---|---|
| | Time p.i. in vivo | | | |
| | 2 min | | 60 min | |
| | Mean | Std. dev. | Mean | Std. dev. |
| | % injected dose/organ | | | |
| Heart | 1.26 | 0.11 | 1.27 | 0.12 |
| Blood | 5.14 | 0.06 | 1.44 | 0.34 |
| Muscle | 26.1 | 5.2 | 28.0 | 5.4 |
| Lung | 1.36 | 0.16 | 0.99 | 0.19 |
| Liver | 20.2 | 1.8 | 6.16 | 1.71 |
| Liver + GI | 37.5 | 1.5 | 45.0 | 2.8 |
| Kidney + urine | 12.3 | 0.7 | 13.3 | 2.1 |
| | Counts/gram ratio | | | |
| Heart/Blood | 3.58 | 0.2 | 11.6 | 1.9 |
| Heart/Muscle | 5.38 | 1.24 | 4.63 | 2.02 |
| Heart/Liver | 0.84 | 0.14 | 2.71 | 0.97 |
| Heart/Lung | 1.5 | 0.2 | 1.9 | 0.5 |

The complex shows good heart uptake and retention, and good target to non-target ratios in the rat.

EXAMPLE 3

Preparation of
2-[N-(2-Dimethylphosphinoethyl)-2-methoxyethylamino]-1,1-dimethylethanethiol (PL 60)

2-Benzylthio-1-nitro-2-methylpropane

Acetone (25 g), benzyl mercaptan (53 g), nitromethane (26.2 g), and piperidine (8 cm$^3$) were dissolved in benzene (150 cm$^3$) and the mixture heated under reflux with azeotropic removal of water. After 48 h the reaction mixture was allowed to cool and washed first with dilute hydrochloric acid, then with water. The remaining solution was dried (MgSO$_4$) and the solvent then removed under reduced pressure to give the nitro system (76.5 g, 85%). This material was sufficiently pure to be used without further purification.

$\delta_H$(CDCl$_3$; 270 MHz) 1.46(6H, s), 3.77(2H, s), 4.38(2H, s), 7.2–7.35(5H, m).

$\delta_C$(CDCl$_3$) 26.4(×2), 33.4, 44.3, 84.8, 127.3, 128.7(×2), 129.0(×2), 137.0.

2-Benzylthio-2-methylpropylamine

A solution of 2-benzylthio-1-nitro-2-methylpropane (19 g) in dry ether (75 cm$^3$) was added dropwise over a period of about 1 h to a stirred suspension of lithium aluminium hydride (9.6 g) in dry ether (500 cm$^3$), cooled in an ice bath. When the addition was complete the mixture was heated under reflux for an additional hour. Excess lithium aluminium hydride was destroyed by the careful addition of water, and then an aqueous solution of sodium potassium tartrate (500 cm$^3$, 20% w/w) was added. The mixture was stirred until the solids had dissolved and the ether layer was then separated. The aqueous solution was then extracted with ether (3×50 cm$^3$) and the combined extracts then dried (MgSO$_4$). Removal of the ether under reduced pressure gave the crude product which was purified via recrystallisation of its hydrochloride salt from isopropanol. The purified amine (7.5 g, 46%) was obtained as a yellow oil.

$\delta_H$(CDCl$_3$; 270 MHz) 1.27(6H, s), 1.71(2H, br s), 2.61(2H, s), 3.67(2H, s), 7.2–7.4(5H, m).

$\delta_C$(CDCl$_3$) 26.0(×2), 32.2, 48.2, 51.2, 126.5, 128.1(×2), 128.4(×2), 138.0.

N-(2-Dimethylphosphinothioylethyl)-2-benzylthio-2-methylpropylamine

A mixture of 2-benzylthio-2-methylpropylamine (5 g) and dimethylvinylphosphine sulphide (6 g) in ethanol (120 cm$^3$) was heated under reflux for 4 days. The solvent was removed and the crude product purified by chromatography on florisil using ethyl acetate-petroleum ether (b.p. 60°–80° C.) mixtures as eluant. The pure phosphine sulphide (5 g, 62%) was obtained as a pale yellow oil $\delta_P$(CDCl$_3$) 36.1

$\delta_H$(CDCl$_3$; 270 MHz) 1.32(6H, s), 1.74(6H, d, $J_{PH}$ 13 Hz), 1.97(2H, dt, $J_{HH}$ 7 Hz, $J_{PH}$ 12 Hz), 2.48(2H, s), 2.83(2H, dt, $J_{HH}$ 7 Hz, $J_{PH}$ 15 Hz), 3.69(2H, s), 7.2–7.4(5H, m).

$\delta_C$(CDCl$_3$) 21.5(×2)(d, $J_{PC}$ 54 Hz), 27.4(×2), 32.7, 34.8(d, $J_{PC}$ 53 Hz), 43.9(d, $J_{PC}$ 3 Hz), 47.0, 58.9, 126.7, 128.3(×2), 128.6(×2), 138.6.

N-(2-Benzylthio-2-methylpropyl)-N-(2-dimethylphosphinothioylethyl)methoxyacetamide Methoxyacetyl chloride (1.03 g) in dry toluene (10 cm$^3$) was added dropwise to a stirred solution of N-(2-dimethylphosphinothioylethyl)-2-benzylthio-2-methylpropylamine (3 g) and pyridine (1.2 cm$^3$) in dry toluene (70 cm$^3$) at 0° C. After stirring for 1 h the mixture was filtered and the volatile components removed under reduced pressure (40° C. at 0.05 mmHg) to give the amide (2.4 g, 65%) as a yellow oil which solidified on standing. An analytically pure sample of the amide (m.p. 91°–92° C.) was obtained by recrystallisation from ethyl acetate.

Found: C, 55.89; H, 8.03; N, 3.9. C$_{18}$H$_{30}$NO$_2$PS$_2$ requires C, 55.79; H, 7.8; N, 3.61%.

$\delta_P$(CDCl$_3$) 33.7, 35.0 (∼1:1 mixture of rotamers)

$\delta_H$(CDCl$_3$; 270 MHz) 1.36(6H, s), 1.40(6H, s), 1.72(6d, $J_{PH}$ 13 Hz), 1.74(6H, d, $J_{PH}$ 13 Hz), 2.13(2H, m), 2.27(2H, m), 3.42(3H, s), 3.45(3H, s), 3.50(2H, s), 3.53(2H, s), 3.82(2H, s), 3.83(2H, s), 3.83(2H, m), 3.95(2H, m), 4.16(2H, s), 4.21(2H, s), 7.2–7.4(10H, m).

$\delta_C$(CDCl$_3$) 21.17(×2)(d, $J_{PC}$ 54 Hz), 21.23(×2)(d, $J_{PC}$ 54 Hz), 27.4(×2), 27.7(×2), 31.8(d, $J_{PC}$ 51 Hz), 33.3, 33.4, 33.4(d, $J_{PC}$ 49 Hz), 42.8, 43.6, 47.4, 47.9, 53.3, 57.0, 59.2, 59.3, 71.3, 71.9, 126.9, 127.1, 128.5(×2), 128.6(×2), 129.0(×4), 137.5, 138.0, 170.0, 170.6.

N-(2-Dimethylphosphinothioylethyl)-N-(2-methoxyethyl)-2-benzylthio-2-methylpropylamine To a stirred solution of N-(2-benzylthio-2-methylpropyl)-N-(2-dimethylphosphinothioylethyl)methoxyacetamide (750 mg) in dry toluene (10 cm$^3$) at 0° C., under an atmosphere of dry nitrogen was added a solution of boranetetrahydrofuran complex in tetrahydrofuran (5.25 cm$^3$, 1M). The mixture was stirred for 30 min at 0° C. and then for 4 h at room temperature. Concentrated hydrochloric acid (1 cm$^3$) was added carefully and the tetrahydrofuran then removed under reduced pressure. The remaining aqueous solution was made strongly basic by the addition of aqueous sodium hydroxide (6M) and then extracted with chloroform (3×10 cm$^3$). The extracts were dried (Na$_2$SO$_4$) and the solvent removed to give the product (500 mg, 71%) as a yellow oil.

$\delta_P$(CDCl$_3$) 35.6.

$\delta_H$(CDCl$_3$; 270 MHz) 1.31(6H, s), 1.70(6H, d, $J_{PH}$ 13 Hz), 2.08(2H, m), 2.59(2H, s), 2.77(2H, t, $J_{HH}$ 6 Hz), 3.04(2H, m), 3.31(3H, s), 3.47(2H, t, $J_{HH}$ 6 Hz), 3.77(2H, s), 7.2–7.4(5H, m).

$\delta_C$(CDCl$_3$) 20.8(×2)(d, $J_{PC}$ 54 Hz), 26.7(×2), 31.1(d, $J_{PC}$ 51 Hz), 32.7, 47.7, 49.8, 54.5, 58.5, 65.7, 71.3, 126.6, 128.2(×2), 128.7(×2), 138.2.

2-[N-(2-Dimethylphosphinoethyl)-2-methoxyethylamino]-1,1-dimethylethanethiol

A solution of N-(2-dimethylphosphinothioylethyl)-N-(2-methoxyethyl)-2-benzylthio-2-methylpropylamine (500 mg) in dry tetrahydrofuran (10 cm$^3$) was placed in a flask fitted with a low temperature condenser (−50° C.), drying tube and gas inlet. The flask was flushed with nitrogen, the solution cooled to −50° C., and then dry ammonia (40 cm$^3$) was condensed into the flask. Small pieces of sodium were then added to this mixture until the blue colouration persisted for at least 1 hour. The blue colouration was then discharged by the addition of ammonium chloride, and the mixture allowed to warm to room temperature. As the ammonia evaporated steps were taken to ensure that no air entered the apparatus. [The flask and its contents were then transfered to a glove box containing a nitrogen atmosphere for subsequent operations.] The reaction mixture was then filtered and the solvent removed under reduced pressure to give a yellow oil containing some solid material. The oil was dissolved in chloroform, the solid removed by filtration, and the solvent removed under reduced pressure to give 2-[N-(2-dimethylphosphinoethyl)-2-methoxyethylamino]-1,1-dimethylethanethiol as an oil.

$\delta_P$(CDCl$_3$) 54.3

$\delta_H$(CDCl$_3$; 270 MHz) 1.03(6H, d, $J_{PH}$ 2 Hz), 1.32(6H, s), 1.57(2H, m), 2.55(2H, s), 2.77(2H, m), 2.81(2H, t, $J_{HH}$ 6 Hz), 3.34(3H, s), 3.48(2H, t, $J_{HH}$ 6 Hz).

$\delta_C$(CDCl$_3$) 14.0(×2)(d, $J_{PC}$ 13 Hz), 29.3(d, $J_{PC}$ 11 Hz), 30.5(×2), 46.4, 53.4(d, $J_{PC}$ 20 Hz), 54.6, 58.8, 69.3, 71.3.

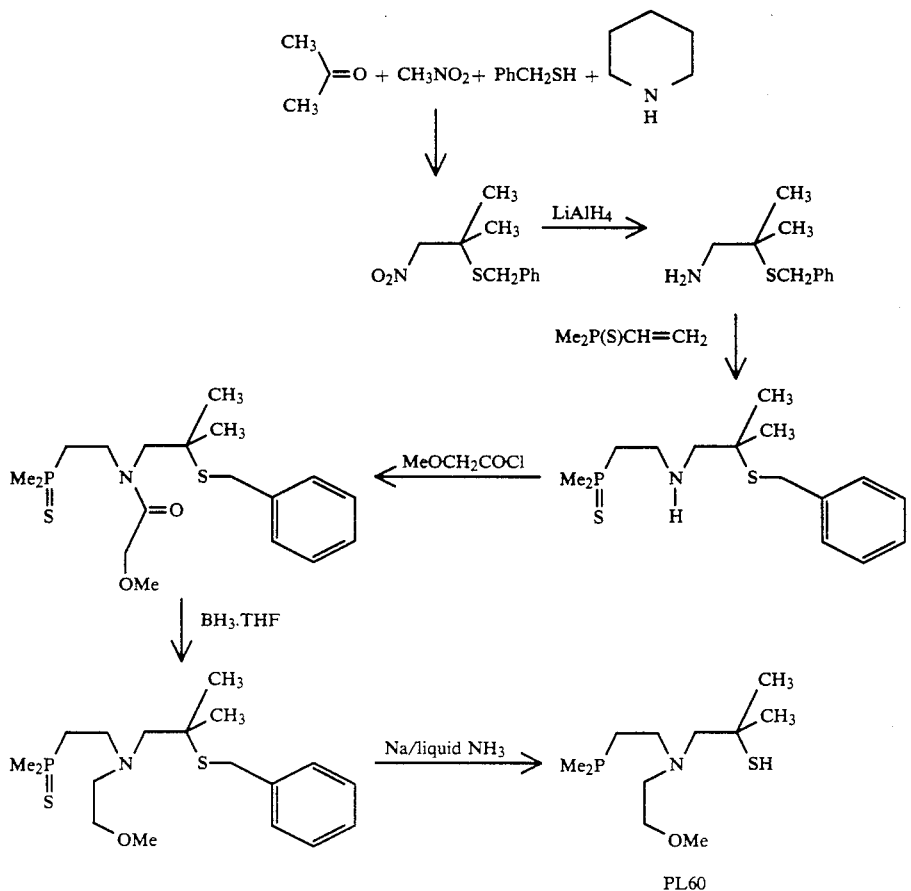

PL60

EXAMPLE 4

Preparation of 2-[N-(2-Dimethylphosphinoethyl)-N-methylamino]-1,1-bis(methoxymethyl)ethanethiol (PL 61)

3-Methoxy-2-methoxymethyl-1-propene

To a solution of sodium methoxide, prepared by adding sodium (11 g) to dry methanol (250 cm³), was added 3-chloro-2-chloromethyl-1-propene (30 g). The resulting mixture was heated under reflux for 18 h, cooled, and then filtered. The filtrate was neutralised by the addition of acetic acid and then diluted by the addition of an equal volume of water. This aqueous solution was extracted with petroleum ether (b.p. 30°-40° C.), the extracts dried, and the solvent removed to give the crude a product which was purified by distillation. 3-Methoxy-2-methoxymethyl-1-propene (18 g, 65%) was obtained as a colourless liquid (b.p. 122° C. at 742 mmHg).

$\delta_C$(CDCl₃) 57.3(×2), 72.7(×2), 112.9, 142.3

1-Bromo-2-hydroxy-3-methoxy-2-(methoxymethyl)propane

3-Methoxy-2-methoxymethyl-1-propene (18 g) was added to a vigorously stirred suspension of N-bromosuccinimide (27.6 g) in water (150 cm³). After stirring for 30 min the suspended solid had dissolved. The reaction mixture was then extracted with diethyl ether, the extracts dried, and the solvent removed under reduced pressure to give the bromohydrin as an oil (30 g, 94%) which was used without further purification.

$\delta_C$(CDCl₃) 35.8, 59.1(×2), 72.6, 73.5(×2).

2,2-Bis(methoxymethyl)oxirane

To 1-bromo-2-hydroxy-3-methoxy-2-(methoxymethyl)propane (30 g) was added sodium hydroxide (5.6 g) in water (50 cm³). The mixture was stirred at room temperature for 1 h and then extracted with diethyl ether. The extracts were dried (Na₂SO₄) and the solvent removed under reduced pressure (40° C. at 15 mmHg) to give the oxirane (13 g, 70%) as a colourless liquid. No further purification of this material was needed.

$\delta_C$(CDCl₃) 48.3, 57.2, 59.2(×2), 72.2(×2).

2,2-Bis(methoxymethyl)thiirane 2,2-Bis(methoxymethyl)oxirane (13 g) was stirred with a solution of potassium thiocyanate (9.7 g) in water (40 cm³) for 18 h at room temperature. The aqueous layer was then replaced with a fresh solution of potassium thiocyanate (9.7 g) in water (40 cm³) and the mixture stirred for a further 6 h. The bulk of the thiirane was then separated from the aqueous layer which was then extracted with diethyl ether. These extracts were combined with the bulk of the thiirane, the solution dried and the solvent removed (40° C. at 15 mmHg) to give the thiirane (13 g, 90%) as a colourless liquid.

$\delta_C$(CDCl₃) 28.0, 44.2, 58.8(×2), 75.6(×2).

1,1-Bis(methoxymethyl)-2-(methylamino)ethanethiol 2,2-Bis(methoxymethyl)thiirane (6 g) was added to a solution of methylamine (12 g) in benzene (80 cm³) and the mixture heated in a Teflon-lined autoclave at 70° C. for 48 h. Volatile components were carefully removed under reduced pressure (40° C. at 100 mmHg) to give the amino-thiol which was used without further purification.

δ_H(CDCl_3: C_6H_6; 270 MHz) 1.9(1H, br s), 2.42(3H, s), 2.71(2H, s), 3.34(6H, s), 3.42–3.50(4H, AB system, $J_{AB}$ 9 Hz)

δ_C(CDCl_3) 36.6, 51.3, 56.1, 58.5, 75.4

2-Benzylthio-3-methoxy-2-methoxymethyl-N-methylpropylamine 1,1-Bis(methoxymethyl)-2-(methylamino)ethanethiol (6 g) was stirred with aqueous sodium hydroxide (60 cm³, 2M) for a short time and then benzyl chloride (4.3 g) was added. This mixture was stirred at room temperature for 3 h and then made slightly acidic (~pH 4) by the addition of dilute hydrochloric acid. The mixture was extracted with chloroform, and the chloroform then removed under reduced pressure to give a viscous oil which gave a solid on trituration with ether. The free amine was liberated from the hydrochloride salt by the addition of saturated aqueous sodium bicarbonate and then extracted into chloroform. The chloroform extracts were dried (Na_2SO_4) and the solvent removed under reduced pressure to give the amine (3.5 g) as a brown oil.

Found: C, 62.16; H, 8.68; N, 4.95. $C_{14}H_{23}NO_2S$ requires C, 62.41; H, 8.60; N, 5.20%. M+269.

δ_H(CDCl_3; 270 MHz) 2.30(3H, s), 2.68(2H, s), 3.32(6H, s), 3.53(4H, s), 3.82(2H, s), 7.2–7.35(5H, m).

δ_C(CDCl_3) 32.2, 36.9, 53.6, 54.6, 59.0, (×2) 74.9(×2), 126.7, 128.2(×2), 128.7(×2), 138.4.

2-Benzylthio-N-(2-dimethylphosphinothioylethyl)-3-methoxy-2-methoxymethyl-N-methylpropylamine A solution of 2-benzylthio-3-methoxy-2-methoxymethyl-N-methylpropylamine (2 g) in ethanol (70 cm³) was heated under reflux with dimethylvinylphosphine sulphide (0.9 g) under dry nitrogen for 12 days. ³¹P n.m.r. spectroscopy indicated that at this point the reaction was about 70% complete. The solvent was removed under reduced pressure and the residue purified by repeated column chromatography on florisil using ethyl acetate-petroleum ether (b.p. 60°–80° C.) mixtures as eluant. The pure product (0.9 g, 34%) was obtained as a white solid, m.p. 74° C.

Found: C, 55.54; H, 8.29; N, 3.46. $C_{18}H_{32}NO_2PS_2$ requires C, 55.50; H, 8.28; N, 3.60%.

δ_P(CDCl_3) 35.3

δ_H(CDCl_3; 270 MHz) 1.72(6H, d, $J_{PH}$13 Hz), 2.08(2H, m), 2.35(3H, s), 2.69(2H, s), 2.86(2H, m), 3.34(6H, s), 3.52(4H, s), 3.91(2H, s), 7.2–7.35(5H, m).

δ_C(CDCl_3) 21.0(×2)(d, $J_{PC}$54 Hz), 31.8(d, $J_{PC}$51 Hz), 32.7, 44.0, 53.1, 54.6, 59.0(×2), 59.7, 74.4(×2), 126.7, 128.3(×2), 129.0(×2), 138.4.

2-[N-(2-Dimethylphosphinoethyl)-N-methylamino]-1,1-bis(methoxymethyl)ethanethiol A solution of 2-benzylthio-N-(2-dimethylphosphinothioylethyl)-3-methoxy-2-methoxymethyl-N-methylpropylamine (450 mg) in dry tetrahydrofuran (10 cm³) was placed in a flask fitted with a low temperature condenser (−50° C.), drying tube and gas inlet. The flask was flushed with nitrogen, the solution cooled to −50° C., and then dry ammonia (40 cm³) was condensed into the flask. Small pieces of sodium were then added to this mixture until the blue colouration persisted for at least 1 hour. The blue colouration was then discharged by the addition of ammonium chloride, and the mixture allowed to warm to room temperature. As the ammonia evaporated steps were taken to ensure that no air entered the apparatus. [The flask and its contents were then transfered to a glove box containing a nitrogen atmosphere for subsequent operations.] The reaction mixture was then filtered and the solvent removed under reduced pressure to give a yellow oil containing some solid material. The oil was dissolved in chloroform, the solid removed by filtration, and the solvent removed under reduced pressure to give 2-[N-(2-dimethylphosphinoethyl)-N-methylamino]-1,1-bis(methoxymethyl)ethanethiol as a white solid.

δ_P(CDCl_3) −54.4

δ_C(CDCl_3) 14.0(×2)(d, $J_{PC}$12 Hz), 29.7(d, $J_{PC}$10 Hz), 44.2, 51.9(br s)*, 56.5(d, $J_{PC}$18 Hz), 58.9, 63.2(br, s)*, 67.0(×2) [*peaks begin to sharpen at 50° C.]

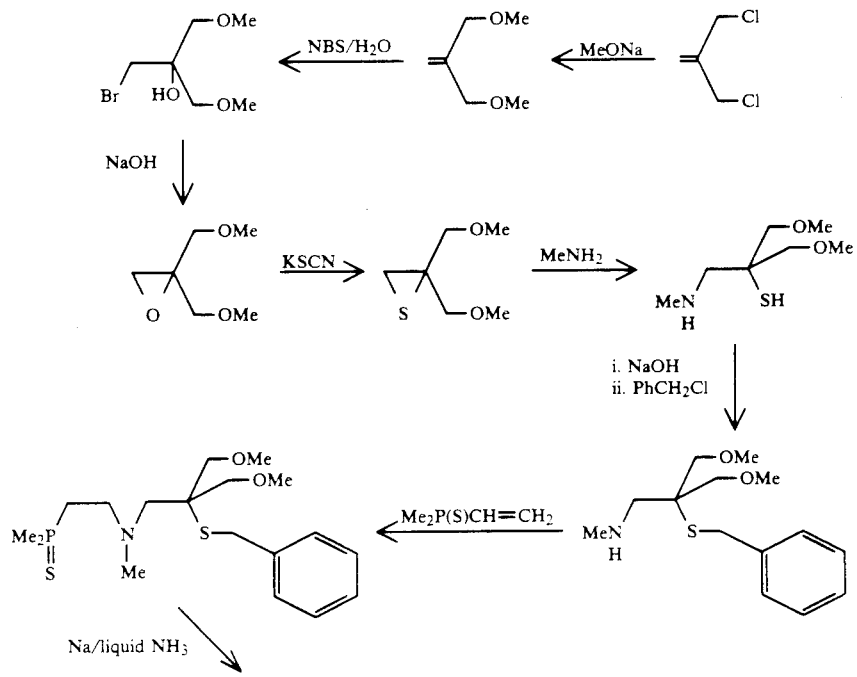

-continued

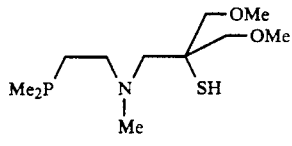

PL61

EXAMPLE 5

Preparation of 4-Mercaptothio-4-[N-(2-dimethylphosphinoethyl)-N-methylaminomethyl]-2,3,5,6-tetrahydro-4H-pyran (PL 62)

4-Benzylthio-2,3,5,6-tetrahydro-4-nitromethyl-4H-pyran 2,3,5,6-Tetrahydropyran-4-one (5 g), benzyl mercaptan (6.2 g), nitromethane (2.7 cm$^3$), and piperidine (1 cm$^3$) were dissolved in benzene (50 cm$^3$), and the mixture heated under reflux with azeotropic removal of water. After 8 days the reaction mixture was allowed to cool and washed first with dilute hydrochloric acid, then with water. The remaining solution was dried and the solvent then removed under reduced pressure to give the nitro system (8g, 60%). This material was sufficiently pure to be used without further purification.

$\delta_C$(CDCl$_3$) 32.2, 33.2($\times$2), 47.0, 62.8($\times$2), 84.2, 127.3, 128.6($\times$2), 129.0($\times$2), 136.3

4-Aminomethyl-4-benzylthio-2,3,5,6-tetrahydro-4H-pyran

A solution of 4-benzylthio-2,3,5,6-tetrahydro-4-nitromethyl-4H-pyran (8 g) in dry ether (25 cm$^3$) was added dropwise over a period of about 45 min to a stirred suspension of lithium aluminium hydride (3.8 g) in dry ether (200 cm$^3$), cooled in an ice bath. When the addition was complete the mixture was heated under reflux for an additional hour. Excess lithium aluminum was destroyed by the careful addition of water, and then an aqueous solution of sodium potassium tartrate (200 cm$^3$, 20% w/w) was added. The mixture was stirred until the solids had dissolved and the ether layer was then separated. The aqueous solution was then extracted with ether and the combined extracts then dried (MgSO$_4$). Removal of the ether under reduced pressure gave the crude product which was purified via the recrystallisation of its hydrochloride salt using isopropanol. The purified amine (3.95 g, 59%) was obtained as a colourless liquid.

$\delta_C$(CDCl$_3$) 31.1, 33.5($\times$2), 50.3, 50.6, 63.2($\times$2), 126.7, 128.2($\times$2), 128.5($\times$2), 137.7

4-Benzylthio-4-[N-(2-dimethylphosphinothioylethyl)aminomethyl]-2,3,5,6-tetrahydro-4H-pyran A mixture of 4-aminomethyl-4-benzylthio-2,3,5,6-tetrahydro-4H-pyran (3.95 g) and dimethylvinylphosphine sulphide (3.2 g) in ethanol (60 cm$^3$) was heated under reflux for 8 days. $^{31}$P n.m.r. spectroscopy showed that the reaction mixture contained approximately equal quantities of starting material and product. The solvent was removed and the crude product purified by chromatography on florisil using ethyl acetate-petroleum ether (b.p. 60°–80° C.) mixtures as eluant. The pure product (2.5 g, 40%) was obtained as an oil.

$\delta_P$(CDCl$_3$) 35.9

$\delta_C$(CDCl$_3$) 21.6($\times$2)(d, $J_{PC}$54 Hz), 31.5, 34.8(d, $J_{PC}$53 Hz), 34.8($\times$2), 43.9(d, $J_{PC}$3 Hz), 49.1, 58.1, 63.4($\times$2), 127.0, 128.5($\times$2), 128.8($\times$2), 138.5

4-Benzylthio-4-[N-(2-dimethylphosphinothioylethyl)-N-(methyl)aminomethyl]-2,3,5,6-tetrahydro-4H-pyran A mixture of 4-benzylthio-4-[N-(2-dimethylphosphinothioylethyl)aminomethyl]-2,3,5,6-tetrahydro-4H-pyran (1.1 g), formaldehyde (0.5 cm$^3$, 40%), and sodium cyanoborohydride (0.1 g) was stirred in acetonitrile (10 cm$^3$) acidified by the addition of acetic acid (3–4 drops). The exothermic reaction was stirred for 3 h and then basified by the addition of aqueous sodium hydroxide (2M). The resulting mixture was extracted with chloroform, the extracts dried, and the solvent removed under reduced pressure to give the methylated amine (1 g, 87%) as a yellow oil.

$\delta_P$(CDCl$_3$) 35.3

$\delta_C$(CDCl$_3$) 20.9($\times$2)(d, $J_{PC}$54 Hz), 31.6(d, $J_{PC}$52 Hz), 31.6, 33.0($\times$2), 44.2, 49.5, 53.3, 63.1($\times$2), 67.6, 126.6, 128.2($\times$2), 128.7($\times$2), 137.6

4-Mercapto-4-[N-(2-dimethylphosphinoethyl)-N-(methyl)aminomethyl]-2,3,5,6-tetrahydro-4H-pyran A solution of 4-benzylthio-4-[N-(2-dimethylphosphinothioylethyl)-N-(methyl)aminomethyl]-2,3,5,6-tetrahydro-4H-pyran (500 mg) in dry tetrahydrofuran (10 cm$^3$) was placed in a flask fitted with a low temperature condenser (−50° C.), drying tube and gas inlet. The flask was flushed with nitrogen, the solution cooled to −50° C., and then dry ammonia (40 cm$^3$) was condensed into the flask. Small pieces of sodium were then added to this mixture until the blue colouration persisted for at least 1 hour. The blue colouration was then discharged by the addition of ammonium chloride, and the mixture allowed to warm to room temperature. As the ammonia evaporated steps were taken to ensure that no air entered the apparatus. [The flask and its contents were then transfered to a glove box containing a nitrogen atmosphere for subsequent operations.] The reaction mixture was filtered and the solvent removed under reduced pressure to give a yellow oil containing some solid material. The oil was dissolved in chloroform, the solid removed by filtration, and the solvent removed under reduced pressure to give the phosphine as a colourless oil.

$\delta_P$(CDCl$_3$) −53.8

$\delta_C$(CDCl$_3$) 14.1($\times$2)(d, $J_{PC}$12 Hz), 30.1(d, $J_{PC}$11 Hz), 37.8($\times$2), 44.4, 49.3, 57.1(d, $J_{PC}$19 Hz), 64.1($\times$2), 71.9

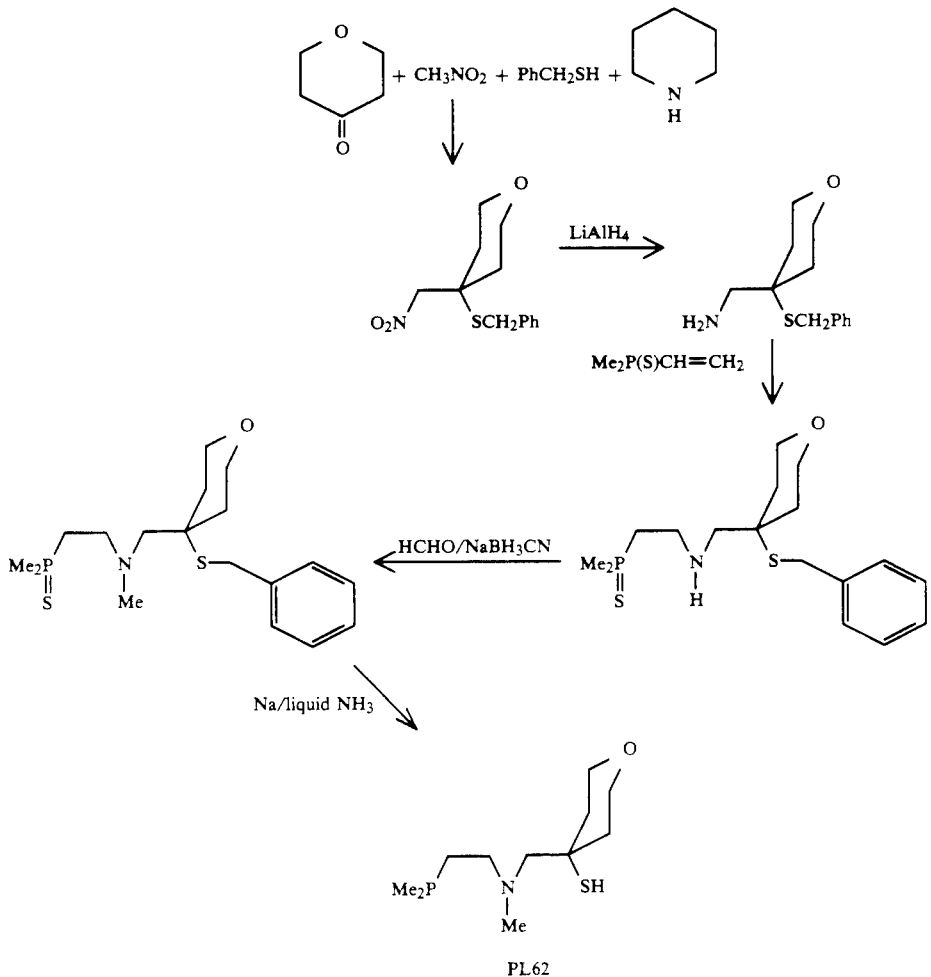

EXAMPLE 6

A Tc-99 m complex of the ligand of Example 3 (PL 60) was formed by the method of Example 2. Animal biodistribution data in rats was obtained by the method of Example 2 and is set out in the following table.

| ANIMAL BIODISTRIBUTION DATA IN RAT (PL60) | | | | |
|---|---|---|---|---|
| | 2 min | | 60 min | |
| | Mean | Std. Dev. | Mean | Std. Dev. |
| % injected dose/organ | | | | |
| Heart | 0.62 | 0.06 | 0.19 | 0.02 |
| Blood | 15.17 | 1.36 | 4.88 | 0.34 |
| Muscle | 21.71 | 2.84 | 8.21 | 0.88 |
| Lung | 2.19 | 0.18 | 0.82 | 0.13 |
| Liver | 31.18 | 3.39 | 13.40 | 0.82 |
| Counts/gram ratio | | | | |
| Heart:Blood | 0.64 | 0.04 | 0.59 | 0.00 |
| Heart:Muscle | 3.32 | 0.35 | 2.63 | 0.11 |
| Heart:Liver | 0.33 | 0.05 | 0.21 | 0.00 |

We claim:

1. A complex with technetium having the formula $[^{99m}Tc^{III}K_2]^+$ where K is a tridentate mono-anionic ligand having the structure $$R_2X\text{-}A\text{-}YR\text{-}Q\text{-}Z$$

where

X is P, As or N,

Y is P, As or N, wherein at least one of X and Y is P or As,

Z is phenolic OH, thiophenol or thiol, each of A and Q is a C1–C4 hydrocarbon bridge, two adjacent C atoms of which may form part of a benzene ring and which may carry at least one C1–C4 alkyl, alkoxy alkyl, alkoxy or tetrahydropyran substituent, R is the same or different at different places in the molecule, and in each case is selected from the group consisting of C1 to C4 alkyl, alkoxy, alkoxyalkyl and alkoxyalkoxy alkyl.

2. The complex as claimed in claim 1, wherein X is P and Y is N.

3. The complex as claimed in claim 1, wherein A is $-C_2H_4-$.

4. The complex of claim 1 wherein the ligand is 1-(N-2'-Dimethylphosphinoethyl-N-methylamino)-2-methylpropane-2-thiol.

5. The complex of claim 1 wherein the ligand is 2-[N-(2-Dimethylphosphinoethyl)-2-methoxyethylamino]-1,1-dimethylethanethiol.

6. The complex of claim 1 wherein the ligand is 2-[N-(2-Dimethylphosphinoethyl)-N-methylamino]-1,1-bis(-methoxymethyl)ethanethiol.

7. The complex of claim 1 wherein the ligand is 4-Mercaptothio-4-[N-(2-dimethylphosphinoethyl)-N-methylaminomethyl]-2,3,5,6-tetrahydro-4H-pyran.

* * * * *